United States Patent [19]

Sugiura et al.

[11] 4,237,266
[45] Dec. 2, 1980

[54] GLUCAN HAVING ANTITUMOR ACTIVITY

[75] Inventors: Mamoru Sugiura, Azatogen, Oazakochino, Konan-shi, Aichi-ken, Japan; Hiroyuki Ohno, Takatsuki, Japan; Yutaro Sasaki, Hirakata, Japan; Kazuaki Hama, Ibaraki, Japan

[73] Assignees: Mamoru Sugiura, Aichi; Hitoshi Itoh, Mie, both of Japan

[21] Appl. No.: 954,242

[22] Filed: Oct. 24, 1978

[30] Foreign Application Priority Data

Oct. 24, 1977 [JP] Japan .................. 52-126743

[51] Int. Cl.³ .......................................... C08B 37/00
[52] U.S. Cl. ...................................... 536/1; 424/180; 435/101
[58] Field of Search ........................................ 536/1

[56] References Cited

U.S. PATENT DOCUMENTS

| | | | |
|---|---|---|---|
| 3,301,848 | 1/1967 | Halleck | 536/1 |
| 3,856,775 | 12/1974 | Fukuoka et al. | 536/1 |
| 3,900,462 | 8/1975 | Komatani et al. | 536/1 |
| 4,075,405 | 2/1978 | Takahashi et al. | 424/180 |
| 4,140,578 | 2/1979 | Yoshikumi et al. | 536/1 |

OTHER PUBLICATIONS

Ono Yakuhin Kogyo Co. Ltd., Abstract 55905V/31 JA-077723 (02-04-74) Japan.

Ono Yakuhin Kogyo (Aman) Abstract 70205V/40 JA-093039 (11-05-74) Japan.

*Primary Examiner*—Johnnie R. Brown
*Attorney, Agent, or Firm*—Young & Thompson

[57] ABSTRACT

A simple glucan has the repeating unit structure

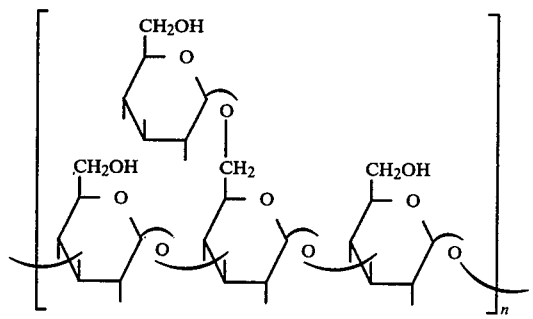

and has a mean molecular weight of about two million. It is produced by culturing mycelia of Coriolus Versicolor Iwade FERM-P No. 2743, and subjecting the cultured medium to hot water extraction, ethanol precipitation, aqueous sodium acetate elution and ion exchange.

1 Claim, 4 Drawing Figures

GLUCAN HAVING ANTITUMOR ACTIVITY

This invention relates to a novel polysaccharide having antitumor activity.

Several antitumor-active substances from Basidiomycetes have been reported. There has been reported previously a process for production of an antitumor substance by culturing *Coriolus Versicolor* of *Basidiomycetes* (Japanese Patent Appln. No. 45-63263); isolation of antitumor substance by enzymatic treatment of *Coriolus Versicolor* (Japanese Patent Appln. No. 47-93039) and a process for manufacture of antitumor substance from culture filtrate of *Coriolus Versicolor* (Japanese Patent Appln. No. 47-77723).

We have now found that, in a hot water extract from cultured mycelia of *Coriolus Versicolor*, one polysaccharide fraction has a high antitumor activity, said fraction being purified to obtain a protein-less novel glucan consisting of $\beta$-1,3-glucosidic linkages as a principal chain having branched chains of $\beta$-1,6-glucosidic linkages.

The object of the present invention is to provide a novel antitumor polysaccharide.

Glycoprotein obtained from water extract of mycelia of *Coriolus Versicolor* is known (Japanese Patent Appln. No. 43-71467). The said extract contains many kinds of complex glycoprotein and there cannot be identified any single antitumor-active substance.

We have found that the aforesaid effective antitumor-active substance can be obtained from the hot water extract as a purified form by ethanol precipitation, aqueous sodium acetate extraction, ethanol reprecipitation, ion-exchange treatment and ethanol fractionation, respectively. Moreover, we have determined the structure of the novel substance.

The polysaccharide of the present invention (hereinafter called this substance or CVG) is a simple glucan consisting of the repeating branched tetra-saccharide unit having $\beta$-1,3-glucosidic linkage as a principal chain in which one glucose residue per three glucose residues of $\beta$-1,3-linkage is linked to each other in $\beta$-1,6-glucosidic linkage, and having a mean molecular weight of about two million.

Figure 1:
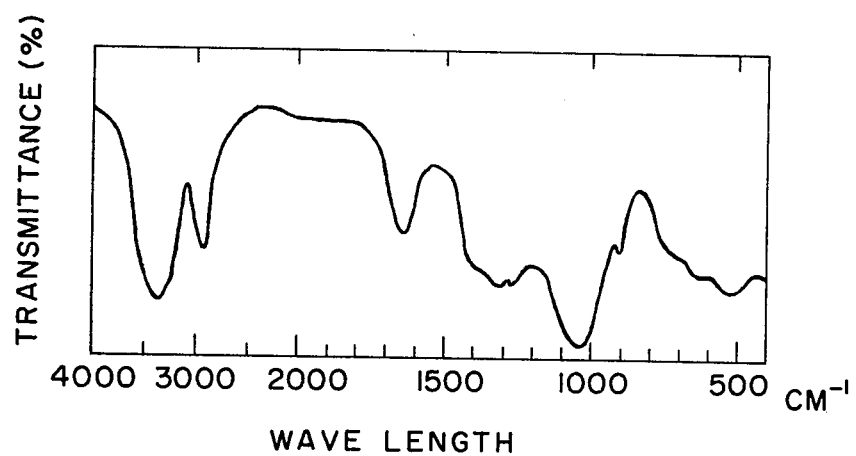
FIG. 1 is the infrared spectrum of the glucan of this invention.

I. Physico-chemical properties:
1. Appearance: white powder.
2. Solubility:
   Insoluble: Organic solvents such as alcohol, acetone, chloroform and pyridine.
   Soluble (up to about 0.5% concentration): Cold water and physiological saline.
   Soluble: Hot water, alkaline solution, formic acid or dimethylsulfoxide.
3. Stability: Stable at 120° C. for 30 minutes steam sterilization without decreasing of antitumor activity. Stable, not hydrolyzed, in 0.5 N sulfuric acid at room temperature for 24 hours with stirring.
4. Elemental analysis: H: 5.67%, C: 38.30.
5. Infrared spectrum (KBr tablet): As shown in FIG. 1, absorption band on glucoside bond at 894 cm$^{-1}$ is confirmed.
6. Specific rotation: $[\alpha]_D^{22} = +22°$ (c=0.2, H$_2$O).
7. Molecular weight: Gel-filtration method.
   >1,500,000 [Gel-filtration by Sephadex G-200 (trademark, Pharmacia Co., Sweden), Bio-Gel p-300 and Bio-Gel A-1.5 m (trademark, Biorad Laboratory Inc., U.S.A.) The same elution patterns were observed by the above gel-filtration comparing with standard marker "Blue dextran 2000" (molecular weight: about two million), whereby the estimated molecular weight of this substance is more than 1,500,000.]
   about 2,000,000 (mean molecular weight) [Gel-filtration using Bio-Gel A-5 m (molecular sieve below M.W. of 5,000,000). Position of the elution was one fraction lower than that of Blue dextran by gel-filtration with deionized water.]
8. Chemical structure:
   (1) Sugar composition:
   D-glucose was the only detectable sugar composition on thin layer chromatogram and gas chromatography after hydrolysis by 2 N-H$_2$SO$_4$ at 100° C. for 5 hours. Glucose content was 98.4–99.8% by the phenol-sulfuric acid method. Ultracentrifugal analysis of this substance was shown as single peak.
   (2) Linkage form of sugar composition:
   This substance was subjected to the usual analytical methods of periodate oxidation, Smith degradation, methylation, acetolysis, mild Smith degradation and methylation analysis, and the chemical structure of this substance was found as consisting of the following repeating unit structure:

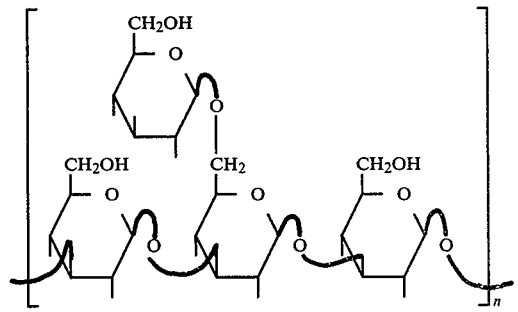

Figure 2:
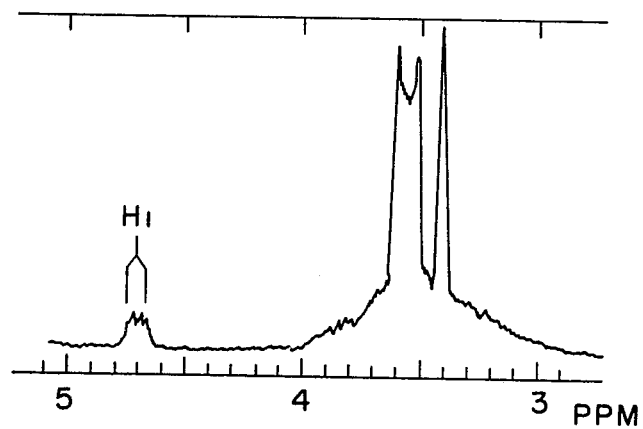
FIG. 2 is the P.M.R. spectrum of the methylated substance.

Proton magnetic resonance (PMR) spectrum (100 MHz) of complete methylated CVG in CDCl$_3$ is shown in FIG. 2. H-1 signal at 4.75 ppm shows that the existence of $\beta$-glucose linkage is confirmed.

II. Biological properties:
1. Toxicity:
   (1) Acute toxicity:
   No mortality was found when maximum tolerable amount of CVG administered p.o. in mice and rats.
   (2) Subacute toxicity:
   No change in general appearance, body weight, food and water intake and general biochemical diagnosis was observed at 100 mg/kg of p.o. administration in mice.
   Increase of weight of thymus was observed in many cases.
   No specific changes were found upon histopathological observation.
2. Cytotoxicity (in vitro):

No cytotoxicity was observed at a concentration of 1 mg/ml on Raji-cells culture.

3. Antitumor effect:

Sarcoma-180 tumor cells were implanted subcutaneously in light axillae of JCL-ICR mice, 5 weeks old, for 3 groups, 8 mice in one group. 24 hours after tumor implantation, the CVG was injected intraperitoneally for two groups. To the control group was administered saline. Results observed three weeks after implantation are shown in the following table:

| Amount Administered (mg/kg) | Route of Administration | Mean Tumor Weight (g ± S.E.) | Inhibition Ratio (%) |
|---|---|---|---|
| Control | i.p. | 2.152 ± 0.491 | |
| 0.1 | i.p. | 1.400 ± 0.718 | 34.9 |
| 1 | i.p. | 0.406 ± 0.211 | 81.1 |

4. Antitumor spectrum:

Growth inhibitory effects including tumor disappearance were observed when CVG was administered in S-180, Ehrlich carcinoma and other solid-tumor-bearing mice, and also this substance was effective against methylcholanthrene-induced pulmonary tumor and spontaneous mammary tumor in mice. These facts reveal that the CVG are effective against not only transplantable tumor but also spontaneous tumor.

Figure 3:
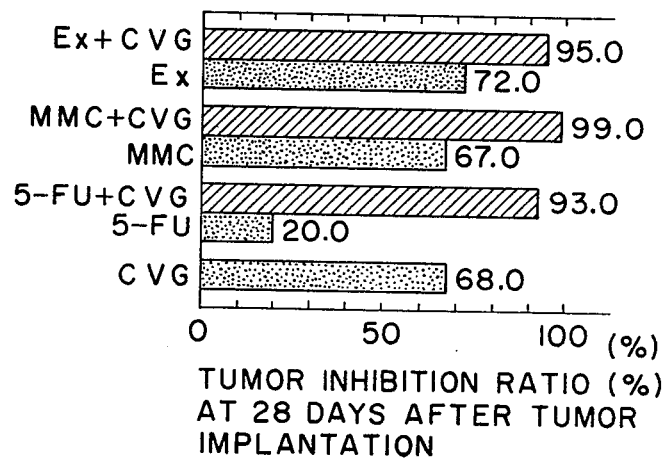
FIG. 3 shows the synergetic effect of this substance and other antitumor substances.

5. Synergetic effect with other antitumor substances:

To Swiss-mice, 10 mice in each group, implanted with sarcoma-180 solid tumor were administered intraperitoneally, twice weekly, mitomycin C (MMC, 1 mg/kg), endoxan (Ex, 20 mg/kg) and 5-fluorouracil (5-FU, 30 mg/kg), each alone or in combination with CVG (1 mg/kg). Tumor inhibition ratio (%) at 28 days after implantation is shown in FIG. 3.

Figure 4:
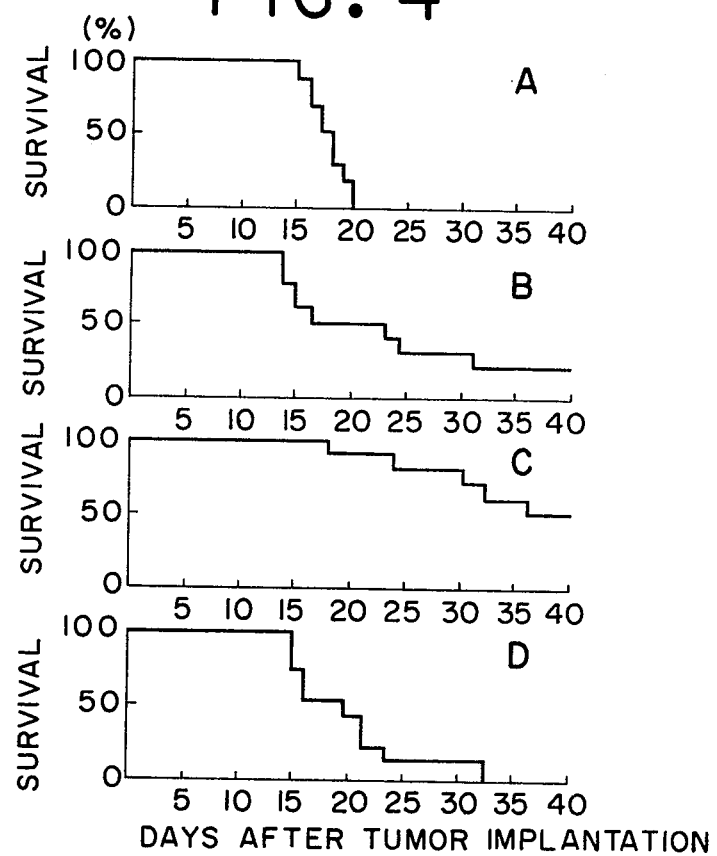
FIG. 4 shows the synergetic effect of this substance and X-ray-irradiated Ehrlich ascites tumor cells.

6. Synergetic effect with X-ray-irradiated Ehrlich ascites carcinoma:

Remarkable tumor growth inhibition was observed when mice, immunized with X-ray-inactivated cells of Ehrlich ascites carcinoma, were administered CVG (20 mg/kg/day), although CVG only is not active against Ehrlich ascites tumor. In FIG. 4 is shown the effect of the combination of inactivated Ehrlich ascites tumor cells and CVG on mice (life prolongation effect).

In FIG. 4:

A: control, Ehrlich ascites carcinoma:
B: immunized with Ehrlich ascites carcinoma only;
C: immunized with Ehrlich ascites carcinoma+CVG; and
D: CVG only.

Production of this substance is generally performed as follows:

Mycelia of *Coriolus Versicolor* was cultured in conventional culture media for *Basidiomycetes*. Cultivation can be performed by submerged aeration culture or solid culture. After cultivation, the mycelia were filtered and were extracted with hot water for five hours to obtain an aqueous soluble extract. To the extract was added four volumes of ethanol to prepare a crude polysaccharide. This crude material was extracted with 0.25 M aqueous sodium acetate and further one-third the volume of ethanol was added therein under cooling to obtain an ethanol precipitate. After dissolving the precipitate in deionized water, the solution was passed through ion-exchanger Duolite A-101 D, Duolite C-20 (trademark, Chemical Process Inc., of U.S.A.) and DEAE-cellulose, respectively, then the ion-exchanger treated solution was subjected to 5-20% ethanol fractionation to yield the purified product CVG.

Purification procedure is shown in the following schema:

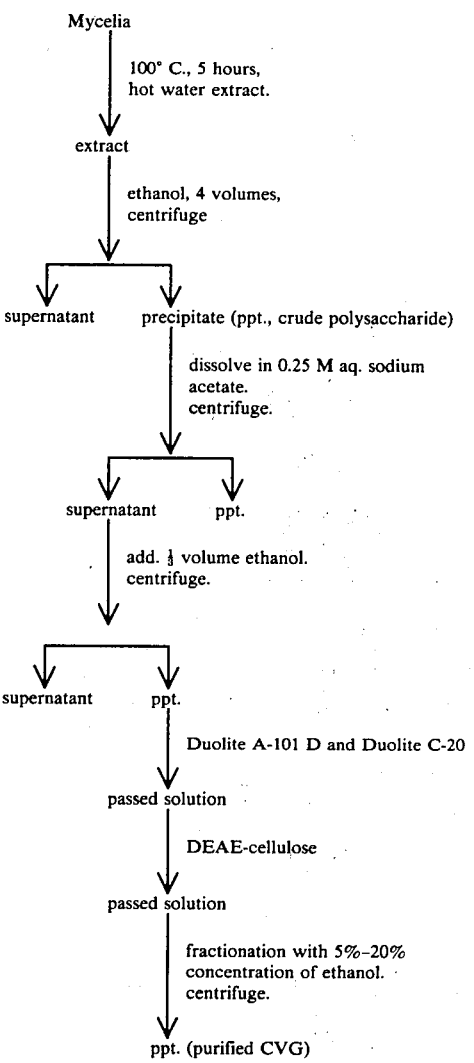

The following example illustrates an embodiment of the present invention but is not to be construed as limiting the invention.

EXAMPLE

To a seed culture medium (100 ml. in culture flask) comprising sucrose 2%, soy sauce 2%, onion extract 0.3%, magnesium sulfate 0.1% and potassium hydrogen phosphate 0.5% was inoculated mycelia of *Coriolus Versicolor* Iwade FERM-P No. 2743 which is U.S. Department of Agriculture deposit No. NRRL 11396, and shake culture for 7 days at 30° C. The seed culture was transferred into the same medium (15 l.) in a jar fermenter and the second seed was cultured for 2 days at 30° C. with agitation of 200 r.p.m., and aeration of 1 v.v.m. After culturing two days, the second seed was transferred into a medium (250 l.) comprising sucrose 5%, soy sauce 5%, onion extract 0.67%, magnesium sulfate 0.05%, potassium hydrogen phosphate 0.1% and silicone 0.1% in a fermentation tank and cultured with agitation of 200 r.p.m. and aeration of 0.5 v.v.m. at 30° C. for 48 hours.

The pH of the culture medium gradually fell from the initial pH of about 5.5 to around pH 3.8 depending on fungal growth, and thereafter rose. The viscosity of the medium increased upon the growth of mycelia. Cultivation was ceased when the culture reached the value of specific viscosity 3.0, pH 4.0 and mycelial amount 1000 mg/100 ml.

The mycelia were collected by centrifugation and extracted with boiling water for 5 hours with stirring, then the insoluble part was removed by centrifugation or filtration to obtain a water-soluble extract. The extract was concentrated under reduced pressure and four volumes of ethanol were gradually added thereto with stirring and the material stood overnight at 5° C. The thus-formed precipitate was completely washed with ethanol and ether, then dried under reduced pressure to obtain crude polysaccharide (127 g). The crude polysaccharide (100 g) was suspended in 0.25 M aqueous sodium acetate (10.1) and dissolved with stirring at ambient temperature in three hours. After removing the insolubles by centrifugation (7,500×g), one-third of the volume of ethanol was added to the supernatant under cooling and the material stood overnight; and the precipitate (14.9 g) was collected by centrifugation.

The precipitate (14.9 g) was dissolved in deionized water (2.1) and was passed through a column of Duolite A-101 D (OH type) followed by a column of Duolite C-10 to obtain a protein-less solution. To this solution was added DEAE-cellulose (OH type), which was treated with 0.5 N NaOH and washed with deionized water to neutrality, then stirred at 5° C. overnight. The solution was filtered through a glass filter.

After adjusting the filtered solution to about 0.2% concentration and adding sodium acetate thereto up to 0.25 M final concentration, cold ethanol was added to 5% (v/v) with cooling in ice-water; then the material was left to stand for three hours. Thereafter this material was centrifuged (15,000×g, 20 min.) at 0° C. to separate the supernatant and precipitate. To the supernatant solution was added cold ethanol to 20% (v/v). After standing for three hours in ice-cold water, the solution was centrifuged at 0° C. to obtain the precipitate.

The precipitate was dialyzed against deionized water and lyophilized to obtain the product (3.52 g).

The purification procedure is shown in the following table:

|  | Yield (g) | Sugar (g) | Protein (g) |
| --- | --- | --- | --- |
| Crude polysaccharide | 100 | 60 | 14 |
| Supernatant of sodium acetate elution | 77 | 57.5 | 8.1 |
| Ethanol fractionation | 14.3 | 12.6 | 1.2 |
| Duolite A-101 D and C-20 treatment | 11.8 | 10.9 | 0.30 |
| DEAE-cellulose treatment | 7.4 | 7.29 | 0.056 |
| Ethanol fractionation | 3.52 | 3.49 | — |

From a consideration of the foregoing disclosure, therefore, it will be evident that the initially recited objects of the present invention have been achieved.

Although the present invention has been described, and illustrated in connection with a preferred embodiment, it is to be understood that modifications and variations may be resorted to without departing from the spirit of the invention, as those skilled in the art will readily understand. Such modifications and variations are considered to be within the purview and scope of the present invention as defined by the appended claims.

What is claimed is:

1. A glucan having a basic repeating unit structure

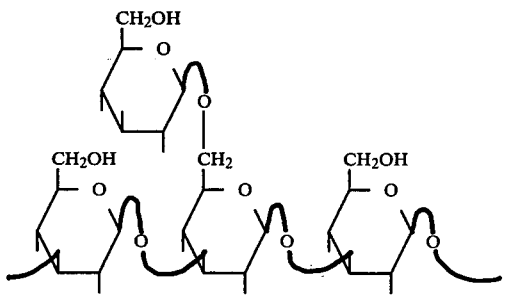

and an estimated molecular weight of about two million.

* * * * *